United States Patent [19]
Collins et al.

[11] Patent Number: 5,434,086
[45] Date of Patent: Jul. 18, 1995

[54] METHOD OF TESTING POTENTIAL CYSTIC FIBROSIS TREATING COMPOUNDS USING CELLS IN CULTURE

[75] Inventors: Francis S. Collins; Mitchell L. Drumm; David C. Dawson, all of Ann Arbor; Daniel J. Wilkinson, Ypsilanti, all of Mich.

[73] Assignee: The Regents of the University of Michigan, Ann Arbor, Mich.

[21] Appl. No.: 164,636

[22] Filed: Dec. 9, 1993

Related U.S. Application Data

[63] Continuation of Ser. No. 769,869, filed as PCT/US91/06660, Sep. 16, 1991, abandoned, which is a continuation-in-part of Ser. No. 584,275, Sep. 18, 1990, Pat. No. 5,240,846, which is a continuation-in-part of Ser. No. 401,609, Aug. 31, 1989, abandoned, which is a continuation-in-part of Ser. No. 399,945, Aug. 24, 1989, abandoned, which is a continuation-in-part of Ser. No. 396,894, Aug. 22, 1989, abandoned.

[51] Int. Cl.$^6$ ............................................ G01N 33/00
[52] U.S. Cl. .................................... 436/125; 435/63; 514/47; 514/263; 514/264; 514/267; 536/26.13
[58] Field of Search ................ 514/47, 263, 264; 536/26.13; 436/125

[56] References Cited

U.S. PATENT DOCUMENTS 5,240,846  8/1993  Collins et al. ................. 435/240.1
5,366,977  11/1994  Pollard et al. ................. 514/263

FOREIGN PATENT DOCUMENTS

WO9404671  3/1994  WIPO ................. 435/172.1

OTHER PUBLICATIONS

Boat et al.(I), "Cystic Fibrosis," Ch. 108 in *Metabolic Basis of Inherited Disease*, McGraw-Hill, New York, 1989, pp. 2649–2680.
Cutting et al., "A Cluster of Cystic Fibrosis Mutations in the First Nucleotide-Binding Fold of the Cystic Fibrosis Conductance Regulator Protein," *Nature*, 366–369 (1990).
Kerem et al. (I), "The Relationship Between Genotype and Phenotype in Cystic Fibrosis—Analysis of the Most Common Mutations($\Delta F_{508}$)," *N. Engl. J. Medicine*, 323(22), 1517–1522 (1990).
Osborne et al., "A Mutation in the Second Nucleotide Binding Fold of the Cystic Fibrosis Gene," *Am. J. Hum. Genetics*, 48, 6089–6122 (1991).
White et al., "A Frame-Shift Mutation in the Cystic Fibrosis Gene," *Nature*, 344, 665–667 (1990).
Ianuzzi et al., "Two Frameshift Mutations in the Cystic Fibrosis Gene," *Am. J. Hum. Genetics*, 48, 227–231 (1991).
Dean et al., "Multiple Mutations in Highly Conserved Residues Are Found in Mildly Affected Cystic Fibrosis Patients," *Cell*, 61, 863–870 (1990).
Boat et al. (II), "Human Respiratory Tract Secretions," *Arch. Biochem. Biophys.*, 177, 95–104 (1976).
Kerem et al. (II), "Identification of the Cystic Fibrosis Gene: Genetic Analysis," *Science*, 245, 1073–1080 (1989).

(List continued on next page.)

*Primary Examiner*—Douglas W. Robinson
*Assistant Examiner*—L. Eric Crane
*Attorney, Agent, or Firm*—Harness, Dickey & Pierce

[57] ABSTRACT

Cystic fibrosis (CF), a lethal genetic disease associated with a defect in Cl transport, is caused by mutations in the gene coding for cystic fibrosis transmembrane conductance regulator (CFTR). Surprisingly, not only wild type CFTR, but several naturally-occurring CFTR mutants carrying a defect in the first nucleotide binding fold (NFB1) all expressed cAMP-activatable Cl currents. Treatment of the CFTR mutants with appropriate concentrations of methylxanthine phosphodiesterase inhibitor (which increases cAMP levels) activated Cl conductance to near wild type levels. The present invention thus provides a new avenue for treating cystic fibrosis by the administration of therapeutically effective amounts of compounds which elevate cAMP levels. Dosage and patient responsiveness to treatment, as well as relative efficacies of the compounds being or to be administered can also be determined in accordance with the methods of present invention.

6 Claims, 4 Drawing Sheets

OTHER PUBLICATIONS

Kobayashi et al., "Benign Missense Variations in the Cystic Fibrosis Gene," *Am. J. Hum. Genetics*, 47, 611–615 (1990).

Kerem et al. (III), "Another Single Amino Acid Deletion in the Putative ATP–Binding Domain of the Cystic Fibrosis Gene Product," *Proc. Nat. Acad. Sci. USA*, 87, 8447–8451 (1990).

Riordan et al., "Identification of the Cystic Fibrosis Gene: Cloning and Characterization of Complementary DNA," *Science*, 245, 1066–1073 (1989).

Rommens et al. (I), "Identification of the Cystic Fibrosis Gene: Chromosome Walking and Jumping," *Science*, 245, 1059–1065 (1989).

Schoumacher et al. (I), "A Cystic Fibrosis Pancreatic Adenocarcinoma Cell Line," *Proc. Nat. Acad. Sci. USA*, 87, 4012–4016 (1990).

Smith, "In Vitro Mutagenesis," *Ann. Rev. Genetics*, 19, 423–462 (1985).

Strong et al., "Cystic Fibrosis Gene Mutation in Two Sisters with Mild Disease and Normal Sweat Electrolyte Levels," *N. Engl. J. Medicine*, 325, 1630–1634 (1991).

Taussig, "Cystic Fibrosis: An Overview," in *Cystic Fibrosis*, Taussig ed., Thiene–Stralton, New York, 1984, pp. 1–9.

Ten Kate, "Carrier Screening for Cystic Fibrosis and Other Autosomal Recessive Diseases," *Am. J. Hum. Genetics*, 47, 359–361 (1990).

Feinberg et al., "A Technique for Radiolabelling DNA Restriction Endonuclease Fragments to High Specific Activity," *Anal. Biochem.*, 132, 6–13 (1983).

Nicholson et al., "Differential Modulation of Tissue Function and Therapeutic Potential of Selective Inhibitors of Cyclic Nucleotide Phosphodiesterase Isozymes," *Trends in Pharmacological Sciences*, 12, 19–27 (1991).

Beavo et al., "Primary Sequence of Cyclic Phosphodiesterase Isozymes and the Design of Selective Inhibitors," *Trends in Pharmacological Sciences*, 11, 150–155 (1990).

Sambrook et al., "Oligonucleotide–Mediated Mutagenesis," Ch. 15 in *Molecular Cloning: A Laboratory Manual, 2nd Ed.*, Cold Spring Harbor Press, Long Island, N.Y., 1989, pp. 15.51–1580.

Anderson et al., "Demonstration that CFTR Is a Chloride Channel by Alteration of Its Anion Selectivity," *Science*, 253, 202–204 (1991).

Cheng et al. (I), "Phosphorylation of the R Domain by cAMP–Dependent Protein Kinase Regulates the CFTR Chloride Channel," *Cell*, 66, 1027–1036 (1991).

Gregory et al.(I), "Expression and Characterization of the Cystic Fibrosis Transmembrane Conductance Regulator," *Nature*, 347, 382–386 (1990).

Boucher et al., "Na+Transport in Cystic Fibrosis Respiratory Epithelia," *J. Clin. Invest.*, 78, 1245–1252 (1986).

Cheng et al. (II), "Defective Intracellular Transport and Processing of CFTR Is the Molecular Basis of Most Cystic Fibrosis," *Cell*, 827–834 (1990).

Cliff et al., "Separate Cl$^-$ Conductances Activated by cAMP and $Ca^{2+}$ in Cl$^-$-Secreting Epithelial Cells," *Proc. Nat. Acad. Sci. USA*, 87, 4956–4960 (1990).

Frizzell, "Cystic Fibrosis: A Disease of the Ion Channels?" *Trends in Neuroscience*, 10(5), 190–193 (1987).

Frizzell et al., "Altered Regulation of Airway Epithelial Cell Chloride Channels in Cystic Fibrosis,".

Cheng et al.(III), "Increased Sulfation of Glycoconjugates by Cultured Nasal Epithelial Cells from Patients with Cystic Fibrosis," *J. Clin. Invest.*, 68–72 (1989).

Gregory et al. (II), "Maturation and Function of Cystic Fibrosis Transmembrane Conductance Regulator Variants Bearing Mutations in Putative Nucleotide–Binding Domains 1 and 2," *Mole. Cell. Biol.*, 11(8), 3886–3893 (1991).

Hyde et al., "Structural Models of ATP–Binding Proteins Associated with Cystic Fibrosis, Multidrug Resistance and Bacterial Transport," *Nature*, 346, 362–365 (1990).

Kartner et al., "Expression of the Cystic Fibrosis Gene in Non–Epithelial Invertebrate Cells Produces a Regulated Anion Conductance," *Cell*, 64, 681–691 (1991).

Knowles et al., "Activation by Extracellular Nucleotides of Chloride Ion Secretion in the Airway Epithelia of Patients with Cystic Fibrosis," *N. Engl. J. Medicine*, 325(8), 533–538 (1991).

Li et al., "Cystic AMP–Dependent Protein Kinase Opens Chloride Channels in Normal But Not in Cystic Fibrosis Airway Epithelial," *Nature*, 321, 358–360 (1988).

Quinton, "Cystic Fibrosis: A Disease in Electrolyte (List continued on next page.)

OTHER PUBLICATIONS

Transport," *FASEB J.*, 4, 2709–2717 (1990).

Rich et al. (I), "Expression of Cystic Fibrosis Transmembrane Conductance Regulator Corrects Defective Chloride Channel Regulation in Cystic Fibrosis Airway Epithelial Cells," *Nature*, 347, 358–363 (1990).

Rich et al. (II), "Effect of Deleting the R Domain on CFTR–Generated Chloride Channels," *Science*, 253, 205–207 (1991).

Rommens et al. (II), "cAMP–Inducible Chloride Conductance in Mouse Fibroblast Lines Stably Expressing the Human Cystic Fibrosis Transmembrane Conductance Regulator," *Proc. Nat. Acad. Sci. USA*, 88, 7500–7504 (1991).

Sato et al., "Defective Beta Adrenergic Response of Cystic Fibrosis Sweat Glands in Vivo and In Vitro," *J. Clin. Invest.*, 73, 1763–1771 (1984).

Schoumacher et al. (II)., "Phosphorylation Fails to Activate Chloride Channels from Cystic Fibrosis Airway Cells," *Nature*, 330, 752–754 (1987).

Tabcharani et al., "Phosphorylation–Regulated Cl− Channel in CHO Cells Stably Expressing the Cystic Fibrosis Gene," *Nature*, 352, 628–631 (1991).

Welsh, "Abnormal Regulation of Ion Channels in Cystic Fibrosis Epithelia," *FASEB J.*, 4, 2718–2725 (1990).

Willumsen et al., "Activation of an Apical Cl− Conductance by $Ca^{2+}$ Ionophores in Cystic Fibrosis Airway Epithelia," *Am. J. Physiology*, 256, C226–C233 (1989).

Venglarik et al., "A Simple Assay for Agonist–Regulated Cl and K Conductances in Salt–Secreting Epithelial Cells," *Am. J. Physiology*, 259, C358–C354 (1990).

Korman et al., "Expression of Human Class II Major Histocompatibility Complex Antigens Using Retrovirus Vectors," *Proc. Nat. Acad. Sci. USA*, 84, 2150–2154 (1987).

Wilson et al. (I), "Correction of DC–18–Deficient Lymphocytes by Retrovirus–Mediates Gene Transfer," *Science*, 248, 1413–1416 (1990).

Wilson et al. (II), "Correction of the Genetic Defect in Hepatocytes from the Watanabe Heritable Hyperlipidemic Rabbit," *Proc. Nat. Acad. Sci. USA*, 85, 4421–425 (1988).

Wilson et al. (III), "Expression of Human Adenosine Deaminase in Mice Reconstituted with Retrovirus–Transduced Hematopoietic Stem Cells," *Proc. Nat. Acad. Sci. USA*, 87, 439–443 (1990).

"Airway Obstruction: Asthma," Ch. 34 in *Merck Manual for Diagnosis and Therapy*, 16th Ed., Berkow et al. eds., Merck Research Laboratories, Rahway, N.J., 1992, pp. 646–657.

TABLE 1.    GENOTYPE VS PHENOTYPE COMPARISONS

| CF Patient Genotype | Sweat Cl | Pulmonary Disease | Pancreatic Status | Reference |
|---|---|---|---|---|
| ΔF508/F508C | Normal | None | Sufficient | Kobayashi et al., *Am. J. Hum. Genet.* 47:611 |
| G551S/G551S | Normal | Mild | Sufficient | Strong et al., Manuscript submitted *N. Engl. J. Med.* (1991) |
| ΔF508/ΔF508 | High | Severe | Insufficient | Kerem et al., *N. Engl. J. Med.*, 323:1512 |
| G551D/G551D | High | Severe | Insufficient | Strong et al., Manuscript submitted *N. Engl. J. Med.* (1991) |

METHOD OF TESTING POTENTIAL CYSTIC FIBROSIS TREATING COMPOUNDS USING CELLS IN CULTURE

SPONSORSHIP

Work on this invention was supported by the Cystic Fibrosis Foundation, the Howard Hughes Medical Institute and by the United States Government under Grant Nos. DK427185, DK39690 and DK29786 awarded by the National Institutes of Health. The Government has certain rights in the invention.

RELATED APPLICATIONS

This is a continuation of United States patent application Ser. No. 07/769,869, filed Oct. 1, 1991, entitled "Treatment of cystic Fibrosis", now abandoned, which is a continuation-in-part application of Ser. No. 584,275, filed Sep. 18, 1990, now U.S. Pat. No. 5,240,846, issued Aug. 31, 1993, entitled "Gene Therapy Vector for cystic Fibrosis," and also filed Sep. 16, 1991 as International Application PCT/US91/06660, which is a continuation-in-part of U.S. application Ser. No. 401,609, entitled "Cystic Fibrosis Gene," filed on Aug. 31, 1989, now abandoned, which is a continuation-in-part of U.S. application Ser. No. 399,945 entitled "Cystic Fibrosis Gene," filed on Aug. 24, 1989, now abandoned, which is a continuation-in-part of U.S. application Ser. No. 396,894, entitled "cystic Fibrosis Gene, filed on Aug. 22, 1989, now abandoned, all of which applications are specifically incorporated by reference herein.

FIELD OF THE INVENTION

The present invention relates generally to the treatment of chloride secretion insufficiencies caused by defects in cystic fibrosis transmembrane conductance regulator (CFTR) with compounds which increase or supplement cyclic AMP (cAMP)levels and, more specifically, to the treatment of cystic fibrosis (CF) with therapeutically effective amounts of phosphodiesterase inhibitors such as methylxanthines.

BACKGROUND OF THE INVENTION

Cystic fibrosis (CF) is the most common lethal autosomal recessive disease among Caucasians, affecting nearly 1 in 2500 newborns. Boat et al., *Metabolic Basis of Inherited Disease.* (McGraw-Hill, N.Y. 1989) 2649-2680. CF is caused by mutations in the gene coding for cystic fibrosis transmembrane conductance regulator (CFTR), a 1480 amino acid protein which has been associated with the expression of chloride conductance in a variety of eukaryotic cell types. See Rommens et al., *Science* 245:1059 (1989); Riorden et al., *Science* 245:1066 (1989); Kerem et al., *Science* 245:1073 (1989); Drumm et al., *Cell* 64:681 (1991); Kartner et al., *Cell* 64:681 (1991); Gregory et al., *Nature* 347:382 (1990); Rich et al., *Nature* 347:358 (1990); Rommens et al., *PNAS* (USA) 88:7500 (1991). Defects in CFTR destroy or reduce the ability of epithelial cells in the airways, sweat glands, pancreas and other tissues to secret Cl in response to cAMP-mediated agonists and impair activation of apical membrane channels by cAMP-dependent protein kinase A (PKA). See Frizell et al., *Trends Neurosci* 10:190 (1987); Welsh, *FASEB J.* 4:2718 (1990).

Although over 100 different mutations have been identified in the CFTR gene, a single NBF1 mutation, the deletion of phenylalanine 508 ($\Delta$F508), accounts for almost 70% of the CF alleles in the population. Kerem et al., *Science* 245:1073 (1989); The Cystic Fibrosis Genetic Analysis Consortium, *Am. J. Hum. Genet.* (1990). Patients homozygous for the $\Delta$F508 mutation present a similar clinical picture, including elevated sweat chloride levels, chronic pulmonary disease, and pancreatic insufficiency and are generally classified as severely affected. Kerem et al., *N. Engl. J. Med.* 323:1 51 7 (1990). The clinical profiles of patients carrying other mutations, however, show a broad spectrum of severity. Kerem et al., *N. Engl. J. Med.* 323:1517 (1990); Cutting et al., *Nature* 346:366 (1990); Osborne et al., *Am. J. Hum. Genet.* 48:608 (1990); White et al., *Nature* 344:665 (1990); Iannuzi et al., *Am. J. Hum. Genet.* 48:226 (1991).

Given the high incidence and devastating nature of this disease, the development of effective CF treatments is imperative. For any therapeutic approach to have a great impact on the CF population, it must also be effective in treating the , $\Delta$F508 mutation, since it is estimated that as many as 92% of CF patients carry at least one $\Delta$F508 allele. Kerem et al., *N. Engl. J. Med.* 323:1517 (1990).

SUMMARY OF THE INVENTION

The present invention provides a method of treatment of chloride secretion insufficiencies caused by CFTR defects generally comprising the administration to the patient of a therapeutically effective amount of a compound, or pharmaceutically acceptable form thereof, which increases or supplements cyclic AMP (cAMP) levels. The method of the invention thus further provides a method of treatment of CF though the administration of therapeutically effective amounts of such compounds, which include phosphodiesterase inhibitors, cAMP and its analogs and $\beta$ adrenergic receptor agonists.

The present invention also provides a method for in vitro dosage determination and screening for CF patient-responsiveness to treatment with the aforementioned compounds. Testing for relative efficacy of these compounds in treating specific CFTR defects and individual patients is also contemplated as falling within the scope of the present invention.

Other features and advantages of the present invention will be become apparent from the following description and appended claims, taken in conjunction with the accompanying drawings.

DETAILED DESCRIPTION OF THE PREFERRED EMBODIMENTS

Cystic fibrosis, a genetic disease associated with a defect in Cl transport, is caused by mutations in the gene coding for cystic fibrosis transmembrane conductance regulator (CFTR), which has been proposed to function as a Cl channel. The functional significance of naturally-occurring, single amino acid mutations in the first nucleotide binding fold (NBF1) of CFTR was investigated by assaying the expression of cAMP-activated Cl conductance in Xenopus oocytes injected with CFTR cRNA. Unexpectedly, oocytes injected with cRNA from several NBF1 mutants, including the most common ΔF508 defect, expressed readily discernable, albeit reduced compared to wild type, Cl currents. Sensitivity of the CFTR mutants to a phosphodiesterase inhibitor (IBMX) and forskolin inversely correlated with the severity of cystic fibrosis in patients carrying the mutations, i.e., mutations associated with severe disease being less sensitive than those associated with mild disease. Even the least sensitive mutants (ΔF508, G551D), however, could be activated to a Cl conductance level approaching that of wild type by increasing the concentration of phosphodiesterase inhibitor (IBMX) and forskolin. These results are consistent with the theory that CFTRs bearing disease-causing mutations in NBF1 are inserted in the plasma membrane, but are defective in their ability to be activated by the appropriate stimulus.

The present invention thus comprises a method of treatment of cAMP-activatable chloride secretion insufficiencies associated with CFTR defects, such as cystic fibrosis, by the administration to the patient of therapeutically effective amounts of a compound, or pharmaceutically acceptable form thereof, which increases or supplements cAMP levels. In accordance with the present invention an increase or supplementation of cAMP levels can be achieved through an increase in cAMP production, inhibition of its breakdown or the administration of supplemental cAMP or analogs thereof. An increase in production, decrease in breakdown or supplementation of cAMP with cAMP or its analogs are hereinafter collectively referred to as "elevation of cAMP levels."

The present invention also provides a method for determining appropriate dosages and relative efficacy of compounds for specific CFTR defects and individual patients, and allows the design and monitoring of appropriate treatments in accordance with the invention. For example, as illustrated in the Specific Examples below, the levels of response for different CFTR mutations may vary with a specific compound. CF patient tissues or cell populations carrying the defect of interest can thus be tested, for example in culture, to assist in determining which type and dosage of compound or combination of compounds are most beneficial for carriers of that mutation or the individual patient.

Preferred compounds for administration in the practice of the method of the invention which elevate cAMP levels include phosphodiesterase inhibitors which increase cAMP levels by inhibiting cAMP breakdown. Supplemental cAMP and analogs thereof or β adrenergic receptor agonists, such as isoproterenol and albuterol, can also be employed in the practice of the invention.

Preferred phosphodiesterase inhibitors which increase cAMP levels include nonspecific inhibitors such as alkylxanthines and cAMP-specific inhibitors such as Rolipram (Shearing AG). A review of phosphodiesterase inhibitors and their selection is presented by Nicholson et al., Trends Pharmacol Sciences 12:19 (1991) and Beavo et al., Trends Pharmacol Sciences 11:150 (1990), which are incorporated herein by reference. Preferred alkylxanthines include the methylxanthines, such as 3-isobutyl-1-methylxanthine (IBMX) and 1,3-dimethylxanthine (theophylline) and other xanthines such as papaverine, pentoxifilline and caffeine. Methylxanthines such as IBMX are most preferred.

Although the aforementioned compounds may be administered alone, they are preferably administered as part of a pharmaceutical formulation. Such formulations can include pharmaceutically acceptable carriers known to those skilled in the art, as well as other therapeutic agents. It will also be appreciated that the compounds of the method of the present invention can be administered in various pharmaceutically acceptable forms, e.g., such as pharmaceutically acceptable salts thereof.

Appropriate dosages of the compounds and formulations administered in accordance with the invention will depend on the type of CFTR mutation and severity of the condition being treated and may also vary from patient to patient. Determining an acceptable or optimal dosage will generally involve the balancing of the level of therapeutic benefit against any risk or deleterious side effects of the dose and treatment of the present invention. For a dose to be "therapeutically effective," it must have the desired effect, i.e., an elevation in cAMP levels as defined herein, resulting in increased Cl secretion by the cell population being or to be treated with the dosage. An optimal dose will be one which, when administered to the patient carrying a CFTR defect, results in Cl secretion at or near wild type CFTR levels.

Administration may be by any suitable route including oral, nasal, topical (including buccal and sublingual), parenteral (including subcutaneous, intramuscular, intravenous and intradermal), vaginal or rectal, with oral and nasal administration being preferred. The formulations thus include those suitable for administration through such routes. It will be appreciated that the preferred route may vary with, for example, the condition and age of the patient. The formulations may conveniently be presented in unit dosage form, e.g., tablets and sustained release capsules, and may be prepared and administered by any methods well known in the art of pharmacy, including liposomal delivery systems.

Formulations of the present invention suitable for oral administration may be presented as discrete units such as capsules, cachets or tablets, as a powder or granules, or as a solution, suspension or emulsion. Formulations suitable for oral topical administration further include lozenges, pastilles, mouthwashes and inhalation mists administered in a suitable base or liquid carrier. Formulations suitable for topical administration to the skin may be presented as ointments, creams, gels and pastes comprising the compound to be administered and a pharmaceutically acceptable carrier or in a transdermal patch.

Formulations suitable for nasal administration wherein the carrier is a solid include powders of a particle size, for example about 20 to 500 microns, which can be administered by rapid inhalation through the nasal passage. Suitable formulations wherein the carrier is a liquid can be administered, for example, as a nasal spray or drops.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit or multi-dose containers, for example, sealed ampules and vials, and may be lyophilized, requiring only the addition of the sterile liquid carrier such as water for injections immediately prior to use. Extemporaneous injection solutions and suspensions may be prepared from sterile powders, granules and tablets of the kind previously described.

Formulations suitable for vaginal administration may be presented as pessaries, tampons, creams, gels, pastes, foams or spray; formulations for rectal administration may be presented as a suppository with a suitable base.

It will be appreciated that in addition to the ingredients specifically mentioned above, the formulations used in the methods of this invention may include other agents conventional in the art having regard to the type of formulation in question.

SPECIFIC EXAMPLES

EXAMPLE 1. Activation of CI Current by Phosphodiesterase Inhibitor.

A. Activation of CI current by IBMX.

Ovarian lobes were removed from anesthetized frogs via a small abdominal incision. Stage V oocytes were separated from follicular membranes by exposure to collagenase (Gibco) and gentle dissection, and were injected with 10–15 ng of cRNA. Three to 12 days after injection, oocytes were assayed for activatable membrane currents by means of two electrode voltage clamps. Outward membrane current was defined as positive. During these experiments, the oocytes were continuously perfused with amphibian Ringers containing 100 mM Na; 106 mM CI; 2.0 mM K; 5 mM HEPES; 1.8 mM Ca and 1.0 mM Mg 100 at pH 7.4. Where indicated, CI was replaced by aspartate.

Figure 1A:
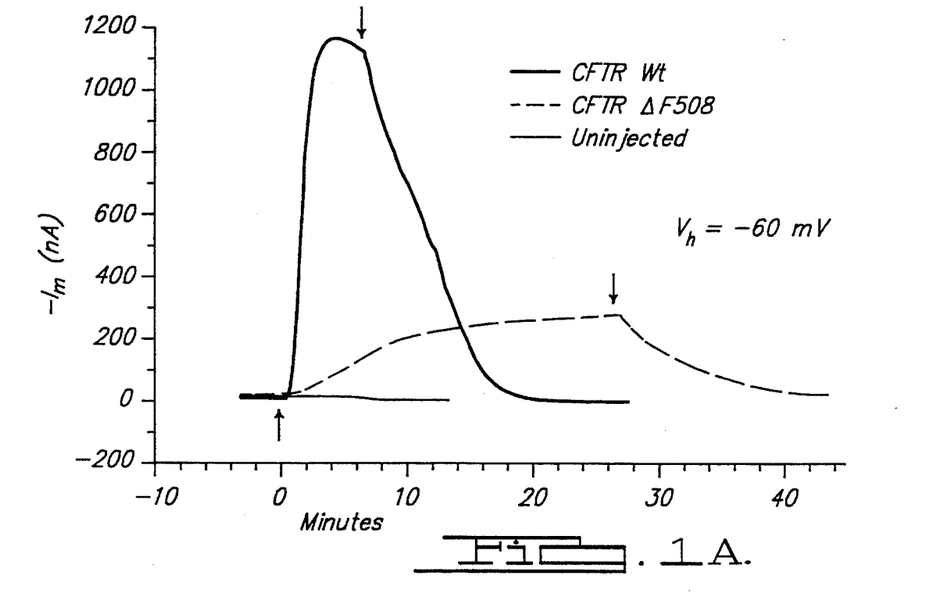
FIG. 1A shows membrane currents at a holding potential of $-60$ mV from oocytes injected with either wild type or $\Delta$F508 cRNA-injected and uninjected oocytes.

Membrane currents ($I_M$) were recorded from Xenopus oocytes at a holding potential ($V_H$) of $-60$ mV. Shown in FIG. 1A are results from oocytes harvested from the same frog on the same day and injected 3 days previously with cRNA transcribed from wild type or ΔF508 CFTR and an uninjected oocyte control. Shown in FIG. 1A is the $I_M$ prior to stimulation, during exposure to a stimulatory cocktail containing 200 μM 8-chlorophenylthio cAMP (8-cpt cAMP), 10 μM forskolin and 1 mM IBMX, and during washout of the cocktail.

As illustrated in FIG. 1A, exposure of the wild type-injected oocyte to the stimulatory cocktail activated a large inward current which reached a maximum value in about 4 minutes, whereas the membrane current in the uninjected oocyte was unaffected. In the ΔF508 injected oocyte, the stimulatory cocktail also induced inward current, but the activation differed markedly from wild type. The rate of increase of $I_M$ was slower and the final steady-state level was significantly lower than wild type. Washing out the forskolin and IBMX reversed the activation and returned both currents to the previous baseline.

B. Effect of Concentration of IBMX on CI Current.

Figure 1B:
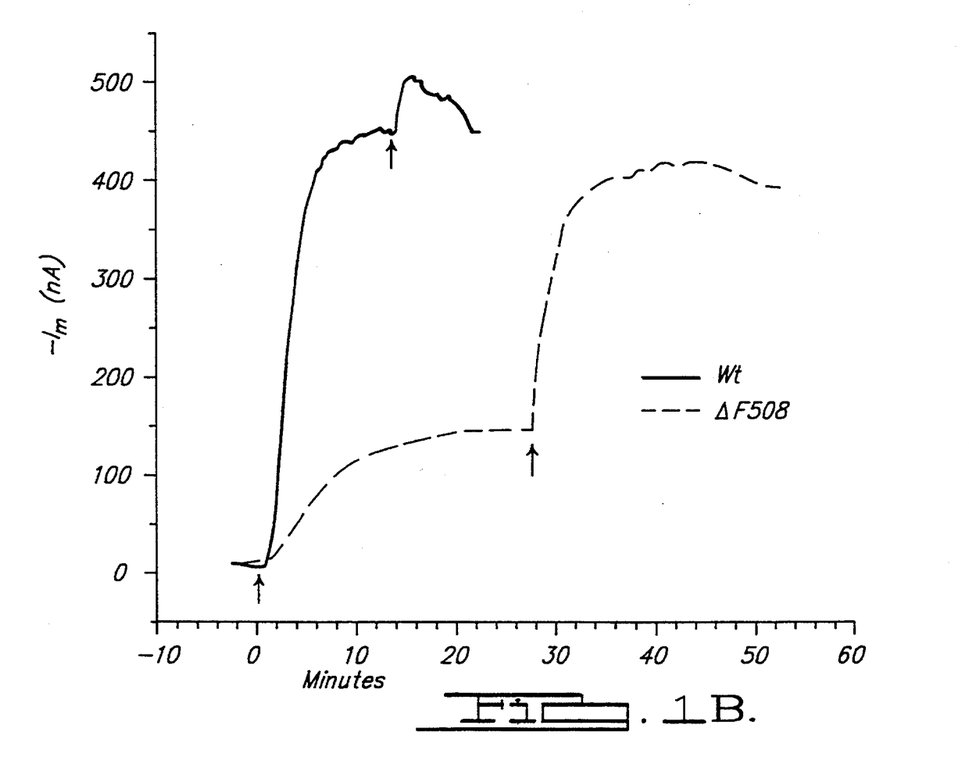
FIG. 1B is a dose response curve comparing the effects of increasing IBMX concentrations on wild type and $\Delta$F508 cRNA-injected oocytes.

Oocytes were harvested from the same frog as described in Example 1A, but about 2 weeks later, and injected with wild type and ΔF508 cRNA. Three days after injection, the oocytes were exposed to a stimulation cocktail containing 10 μM forskolin and, successively, 1 mM and 5 mM IBMX. 8-cpt cAMP was eliminated from the cocktail on the basis of other experiments which showed that it had little effect alone or in combination with forskolin and IBMX. The difference in the currents seen with 1 mM IBMX in FIG. 1A and 1B is typical of the variability seen in expression in oocytes taken from the same frog at different times. As shown in FIG. 1B, raising the concentration of IBMX to 5 mM elevated the current in the ΔF508-injected oocyte to a level comparable to wild type, whereas current in the wild type-injected oocyte was little changed by the same maneuver.

In principle, the reduced current obtained with ΔF508 could be due to altered processing of the mutant protein (Cheng et al., *Cell* 63:827 (1990)) or simply altered sensitivity to the rise in cellular cAMP presumed to occur in response to forskolin and IBMX. The result depicted in FIG. 1B supports the latter explanation.

EXAMPLE 2. Activation of CI Current in Five CFTR Variants.

A. Activation by IBMX.

Figure 4:
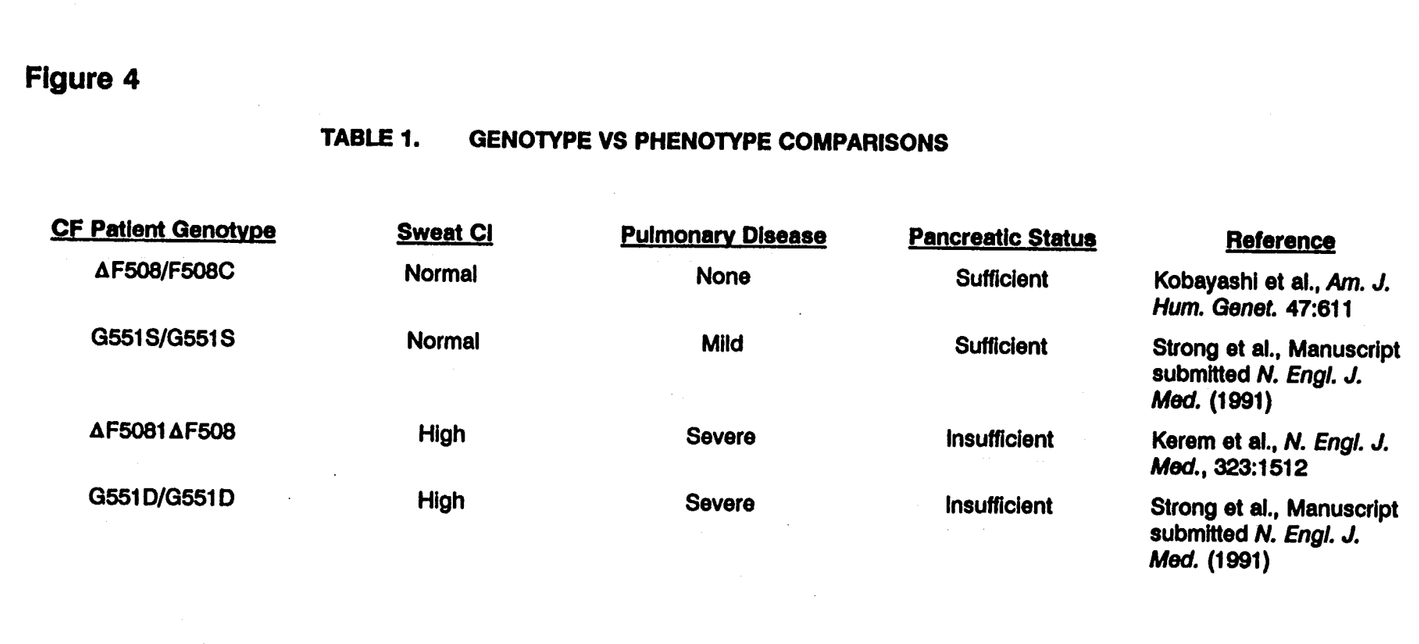
FIG. 4 is a Table comparing CF patient genotype with clinical phenotype.

The striking difference in the sensitivity of oocytes injected with wild type and ΔF508 forms of CFTR cRNA to the stimulatory cocktail prompted us to examine three other naturally occurring CFTR variants for which information pertaining to the severity of disease was available. Table 1, shown in FIG. 4, compares CF patient genotype with clinical phenotype. Patient genotypes are listed in order of disease severity, and are designated by both alleles separated by a/. The ΔF508/F508C compound heterozygotes are clinically unaffected, G551S homozygotes are mildly affected, and the G551D and ΔF508 homozygotes are severely affected.

To facilitate possible comparisons between expression of CI conductance and disease severity, we chose, where possible, mutations found in homozygotes so that only a single mutation contributed to the phenotype. To synthesize CFTR cRNA, 1 μg of linearized plasmid was incubated with 50 U of T7 RNA polymerase (BRL), 40 U RNAsin (Promega), 2 mM each ATP, UTP, CTP, GTP, in buffer supplied by the enzyme manufacturer at 37° C. for 60–90 minutes. RNA was phenol extracted and precipitated, resuspended in $H_2O$. RNA quality and quantity was estimated by comparing to standards on an agarose gel. Mutation constructs were generated by oligonucleotide-mediated sitespecific mutagenesis of 1.7 kb cDNA fragment containing the first third of the CFTR coding sequence. This fragment was cloned into the pSelect Vector (Promega), and oligonucleotides corresponding to the desired mutation were synthesized and used for second strand priming as described by the supplier. After sequencing to verify the presence of the mutation, the fragment was shuttled into a full length cDNA construct in the vector pBluescript (Stratagene).

Figure 2A:
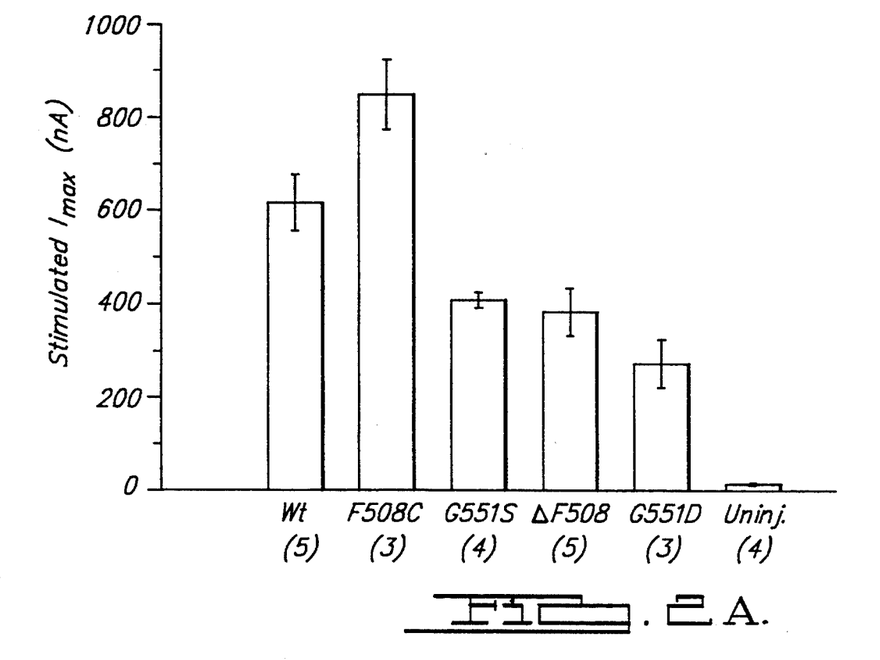
FIG. 2A is a bar graph comparing the maximal currents elicited in oocytes expressing each CFTR variant studied.

FIG. 2A compares the maximal currents activated by forskolin and IBMX for oocytes injected with cRNA representing five forms of CFTR: wild type, F508C, G551 S, ΔF508 and G551D. Maximal responses were defined as current elicited by 5 mM IBMX and 50 μM forskolin. Attempts to utilize higher concentrations of IBMX were compromised by the lack of solubility of the compound in the Ringers. Values are mean ± standard error. As shown in FIG. 2A, if the level of the stimulus is raised sufficiently (10-50 μM forskolin, 5 mM IBMX) even mutants associated with the most severe clinical symptoms exhibit activity which is 50-60% that of wild type.

B. Effects of concentration of IBMX.

Figure 2B:
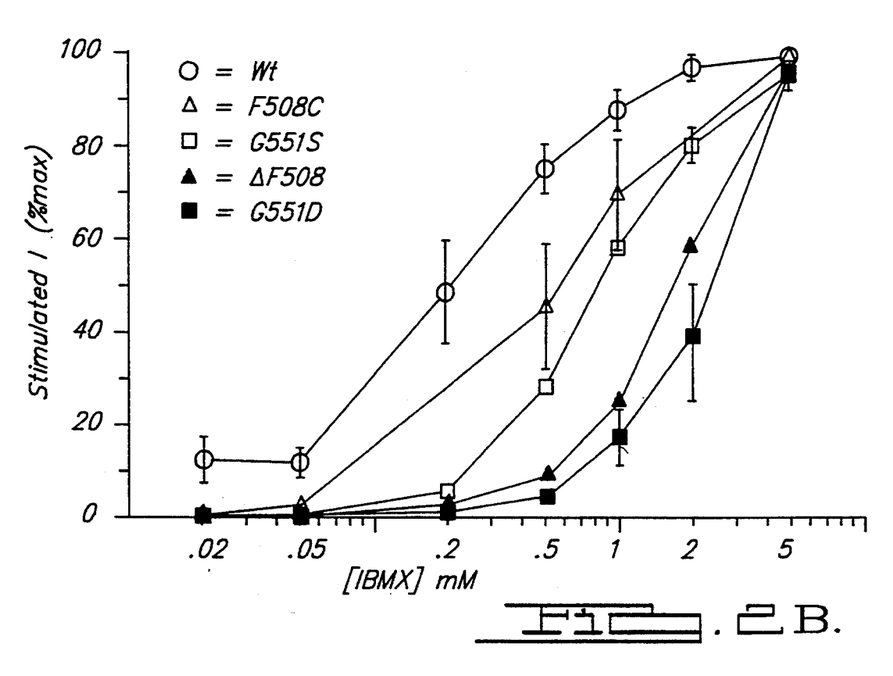
FIG. 2B is a dose response curve showing activated currents (expressed as % activation) for five CFTR variants plotted against the concentration of IBMX in the bath.

Preliminary studies of the response of wild type-injected oocytes indicated that IBMX was the most potent component of the stimulatory cocktail. To circumvent variability between oocytes, each oocyte was exposed to 10 μM forskolin and a series of IBMX concentrations. FIG. 2B shows steady state activated currents for the five CFTR variants described above plotted against the concentration of IBMX in the perfusion solutions expressed as a percent of maximum activation. Values represent mean ± S.E. for 3-5 oocytes (see Example 2A). In some cases the error bars are within the size of the symbol. In each case, the sensitivity of the CFTR variant to IBMX fell as the severity of disease expression in patients increased as shown in Table 1 of FIG. 4.

As expected, oocytes expressing wild type CFTR exhibited the greatest sensitivity to activating conditions. Currents in oocytes expressing F508C, a cysteine for phenylalanine substitution at position 508, were only slightly reduced relative to those seen with wild type. This change has been found in combination with ΔF508 in an unaffected individual and is considered to be neutral. Kobayashi et al., *Am. J. Hum. Genet.* 47:611 (1990). Next in the rank order was G551S, a serine for glycine substitution at position 551, which is associated with mild disease. Strong et al., manuscript submitted to *N. Engl. J. Med.* (1991). Accordingly, the expression of CI conductance, although less than that seen with wild type, was nevertheless substantial at 1 mM IBMX. The greatest reduction in sensitivity was seen with ΔF508 and G551D (an aspartate for glycine substitution), both of which are associated with severe disease. See Strong et al., manuscript submitted to *N. Engl. J. Med.* (1991); Cutting et al., *Nature* 346:366 (1990); Kerem et al., *N. Engl. J. Med.* 323:1517 (1990).

EXAMPLE 3. CI Selectivity of Membrane.

The CI selectivity of the oocyte membranes was examined by comparing current-voltage relations in the presence of normal extracellular CI ($[CI]_o = 106$ mM) to those obtained after reducing $[CI]_o$ to 4 mM.

Figure 3A:
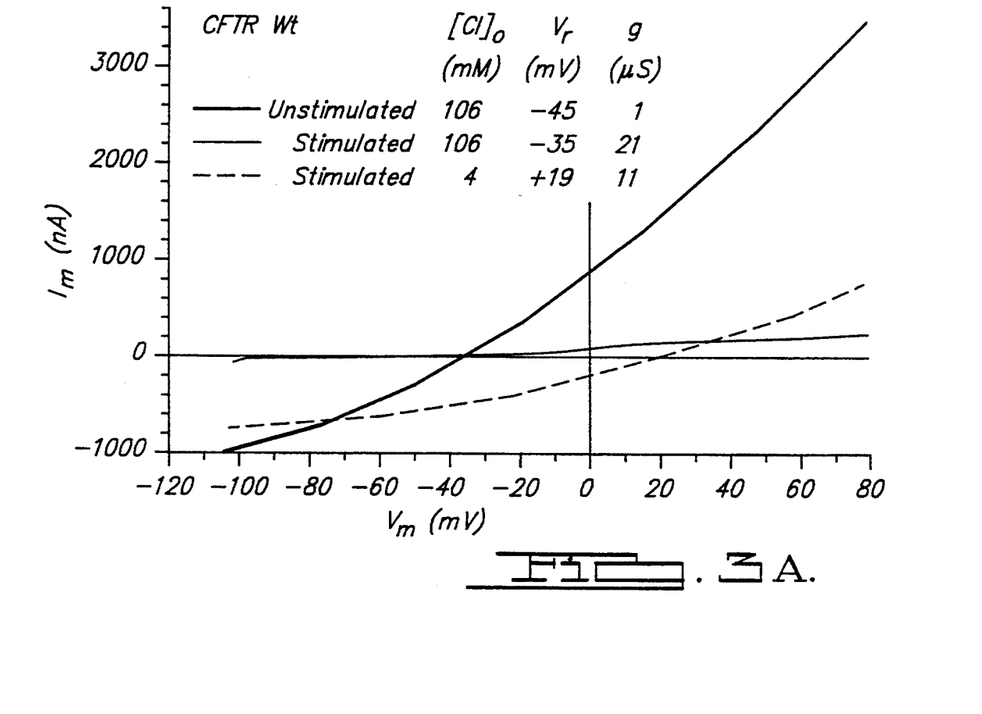
FIG. 3A shows representative I–V plots obtained at maximal activation in oocytes injected with wild type cRNA.
Figure 3B:
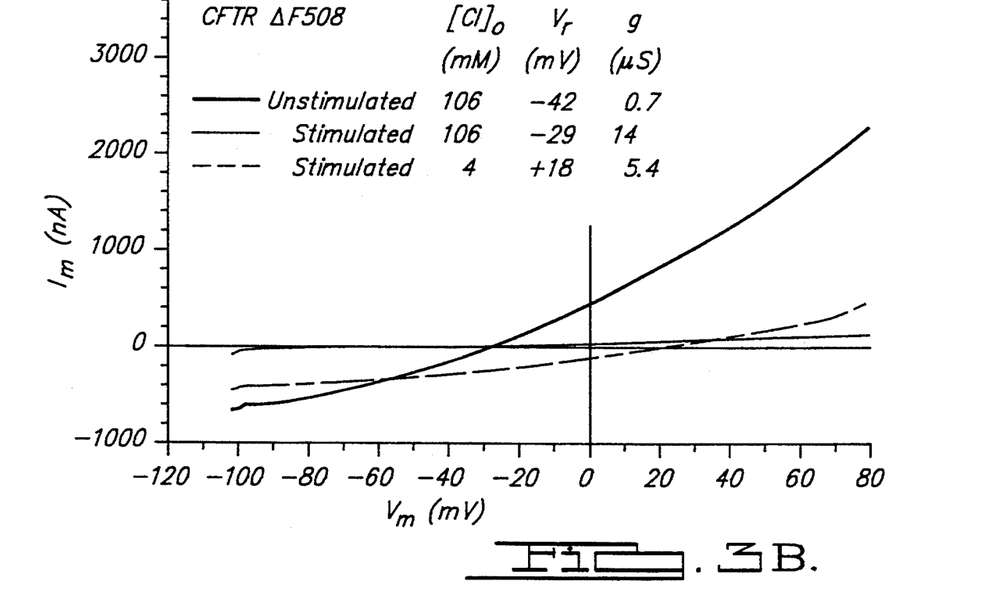
FIG. 3B shows representative I–V plots obtained at maximal activation in oocytes injected with ΔF508 cRNA.

Representative I-V plots were obtained at maximal activation in oocytes injected with either wild type or ΔF508 cRNAs, by ramping the command potential from −100 mV to +80 mV at 100 mV/second. Records were corrected for the small capacitative component of the current. Shown in FIGS. 3A and 3B are records for wild type and ΔF508 cRNA-injected oocytes respectively, obtained prior to activation by forskolin and IBMX, after maximal activation and after reducing $[CI]_o$ from 106 to 4 mM. The small outward current seen in FIG. 3A prior to activation at depolarizing potential was also noted in uninjected oocytes and appears to represent an endogenous CI conductance activated as the result of voltage-dependant $Ca^{2+}$ entry. This current was eliminated in FIG. 3B by perfusing the oocyte with a nominally calcium-free Ringers solution. Because this maneuver had no effect on the activation of $I_M$ in injected oocytes, all I-V relations (except prestimulation in FIG. 3A) were obtained in the $Ca^{2+}$-free condition.

As shown in FIG. 3, reducing $[CI]_o$ shifted the reversal potential in the positive direction by about 50 mV and reduced the conductance for outward current by about 50%. Similar results were obtained with the other mutants (data not illustrated in Figures) indicating that all of these NBF1 mutants were associated with the expression of a CI conductance.

Discussion of Data Presented in Examples.

The data presented in the Examples strongly suggest that the naturally-occurring defects in NBF1 of CFTR examined here do not abolish function, but rather reduce the sensitivity to an activating stimulus. This result has several important implications. First, the similarity in CI conducting properties associated with expression of the five forms of CFTR suggests that, if CFTR functions as a channel as has been proposed (Anderson et al., *Science* 253:202 (1991)), then the conduction pathway per se is not compromised by these mutations. One theory which is consistent with the proposed domain structure of CFTR (Riordan et al. *Science* 245:1066 (1989)) and recent results of site-directed mutagenesis (Anderson et al., *Science* 253:202 (1991)) is that NBF1 is not a part of the anion selective pore. The behavior of naturally-occurring NBF1 mutant CFTRs also strongly suggests that they are detective in their ability to be activated by the appropriate stimulus. Although the normal sequence of events linking stimulus to activation is not completely clear, some of the elements of the transduction process have been identified. Phosphorylation of the R domain by activated subunit of protein kinase A (PKA) appears to be necessary for normal activation of CI conductance in intact cells transfected with wild type CFTR constructs (Cheng et al., *Cell* 66:1027 (1991)); in excised membrane patches from wild type-transfected cells, the presence of PKA and ATP appears to be sufficient for activation of CI channels. Tabcharani et al., *Nature* 352:628 (1991). All of the variants examined here result from single amino acid changes in NBF1, suggesting that although this region does not contain consensus sequences for cAMP-dependent phosphorylation by PKA, it is intimately involved in the transduction process. A similar conclusion was reached regarding an interaction between the R domain and NBF2 (Rich et al., *Science* 253:205 (1991)) in response to forskolin. It has also been reported that CI channels in CF and normal epithelial cells can be activated by application of ATP or UTP to the external apical membrane. Knowles et al., *N. Engl. J. Med.* 325:533 (1991).

In previous studies, introduction of the ΔF508 construct into eukaryotic cells was not associated with the expression of an activated conductance, a result which may reflect inadequate levels of stimulation. Rich et al., *Nature* 347:358 (1990); Rommens et al., *PNAS* (USA) 88:7500 (1991); Gregory et al., *Mol. Cell. Biol.* 11:3886 (1991); Cheng et al., *Cell* 63:827 (1990). In the present experiments, for example FIG. 2A, ΔF508-injected oocytes exposed to 10 μM forskolin did not exhibit readily detectable activation unless the concentration of IBMX exceeded 200 μM. Based on the results presented herein, appropriate pharmacological intervention in accordance with the present invention can increase the activity of mutant CFTRs to ameliorate disease symptoms related to insufficient Cl secretion.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. All publications cited herein are hereby incorporated by reference.

We claim:

1. A method for determination of Cl$^-$ ion secretion responsiveness of a cell population carrying a CFTR defect to a compound selected from the group consisting of a compound which increases the production of cAMP in epithelial cells, a compound which decreases the breakdown of cAMP in epithelial cells, cAMP, an analog of cAMP, or pharmaceutically acceptable forms thereof comprising the steps of:

administering an mount of the compound or its pharmaceutically acceptable form to the cell population;

measuring the change in Cl$^-$ secretion levels in at least a portion of the cell population after administration; and correlating the response observed with those of a baseline control and a normal cell response to an identical concentration of the same compound to determine whether the administered compound is effective to increase Cl$^-$ ion secretion.

2. The method of claim 1, wherein the compound is a phosphodiesterase inhibitor.

3. The method of claim 2, wherein the phosphodiesterase inhibitor is an alkylxanthine.

4. The method of claim 2, wherein the phosphodiesterase inhibitor is cAMP-specific.

5. The method of claim 1, further comprising the step of dosage selection, the dosage selection step further comprising the steps of:

administering a preselected dosage of the compound to the cell population;

comparing the change in Cl$^-$ secretion levels to the change in Cl$^-$ secretion levels after of administration to the same or a comparable cell population of a different preselected dosage of the compound; and selecting the preferred dosage.

6. The method of claim 1, wherein the cell population is an in vitro cell population from a human with cystic fibrosis.

* * * * *